US00PP23093P3

(12) United States Plant Patent
Harris

(10) Patent No.: US PP23,093 P3
(45) Date of Patent: Oct. 2, 2012

(54) AZALEA PLANT NAMED 'MNIHAR011'

(50) Latin Name: ***Rhododendron* sp.**
Varietal Denomination: MNIHAR011

(75) Inventor: James O. Harris, Lawrenceville, GA (US); Ella Ruth Harris, legal representative, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 142 days.

(21) Appl. No.: 12/807,053

(22) Filed: Aug. 25, 2010

(65) Prior Publication Data

US 2012/0054933 P1 Mar. 1, 2012

(51) Int. Cl.
*A01H 5/00* (2006.01)

(52) U.S. Cl. ..... Plt./240

(58) Field of Classification Search ..... Plt./240, Plt./239, 238

See application file for complete search history.

*Primary Examiner* — Kent L Bell

(74) *Attorney, Agent, or Firm* — Jondle & Associates, P.C.

(57) ABSTRACT

A new and distinct variety of Azalea plant with spring, summer, and fall blooming, attractive, showy, dark rose colored hose-in-hose flowers, easily propagated by semi-hardwood cuttings in late spring through summer, moderate growth rate under normal fertilization and moisture conditions; low growing, dense, and compact nature, grows well in containers, thrives in shade or sun and is hardy in Zone 6, is disclosed.

2 Drawing Sheets

Genus and species: *Rhododendron* sp.
Variety denomination: 'MNIHAR011'.

BACKGROUND OF THE NEW PLANT

The present invention is a new and distinct variety of evergreen Azalea of the genus *Rhododendron*. This new Azalea, hereinafter referred to as 'MNIHAR011', was discovered in 2004 in Lawrenceville, Ga. 'MNIHAR011' originated from a planned cross hybridization in 1999 between the female azalea plant 'Conleb' (U.S. Plant Pat. No. 10,581) and the male azalea plant 'Jay Valentine' (unpatented) in a controlled environment in Lawrenceville, Ga. The present invention has a blooming period in spring, summer, and fall, dense, low-growing growth habit, and cold hardiness.

The new variety was first propagated via semi-hardwood cuttings in 2004 in Dearing, Ga. and has been asexually reproduced repeatedly by semi-hardwood cuttings in Dearing, Ga. for over six years. 'MNIHAR011' has been found to retain its distinctive characteristics through successive asexual propagations via semi-hardwood cuttings.

Plant Breeder's Rights for this variety have not been applied for. 'MNIHAR011' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring, summer, and fall blooming;
2. Attractive, showy, dark rose-colored flowers;
3. Numerous hose-in-hose flowers;
4. Easily propagated by semi-hardwood cuttings in late spring through summer;
5. Moderate growth rate under normal fertilization and moisture conditions;

6. Dense, low growing and compact nature;
7. Grows well in containers;
8. Thrives in shade or sun; and
9. Hardy in Zone 6.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of 6-year-old plants that are grown in filtered shade in September in 2009 in Dearing, Ga.

DETAILED BOTANICAL DESCRIPTION OF THE NEW PLANT

Figure 1:
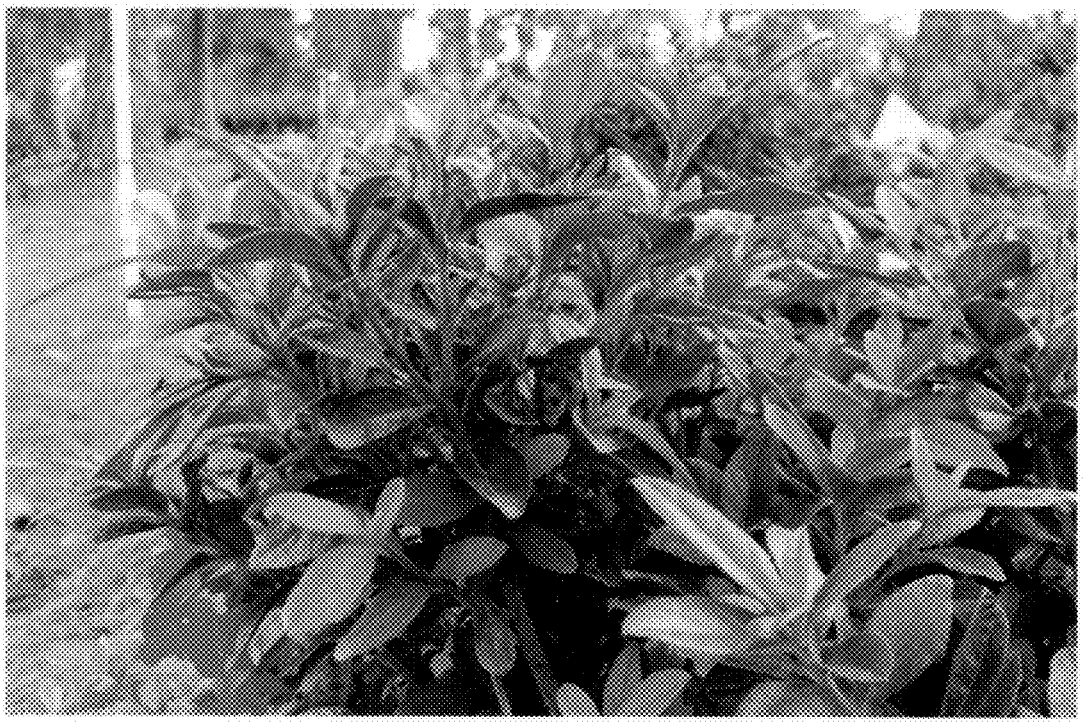
FIG. 1 is a close-up showing stems and mature foliage.
Figure 2:
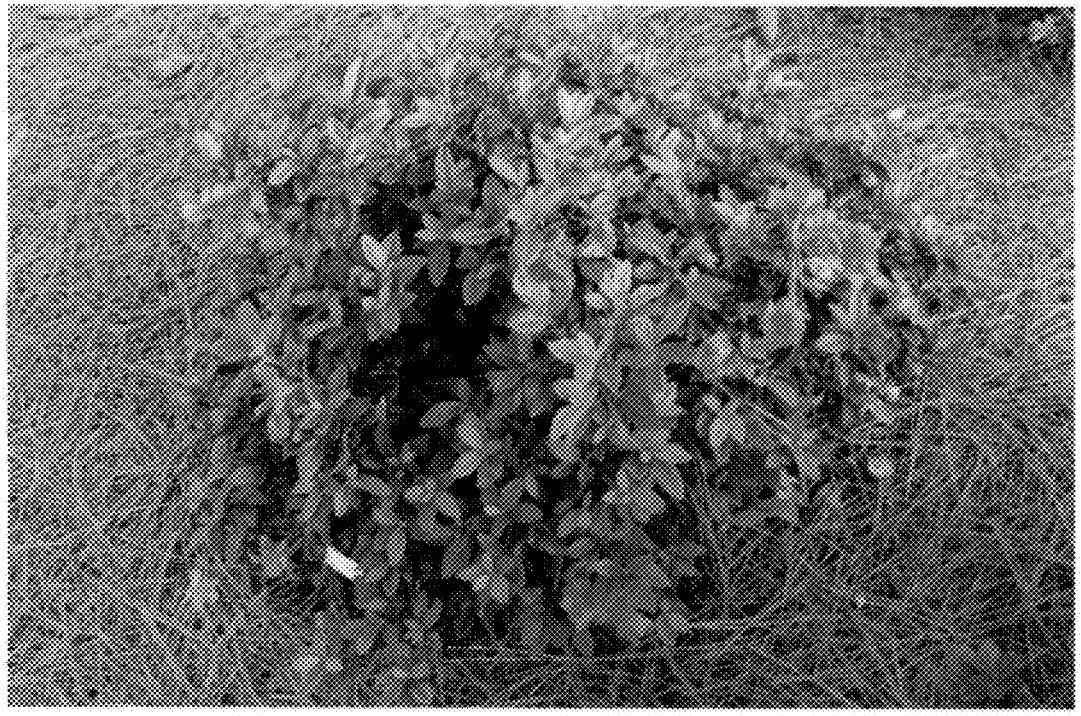
FIG. 2 shows the mature foliage and the whole plant growth habit of a 6-year-old plant.
Figure 3:
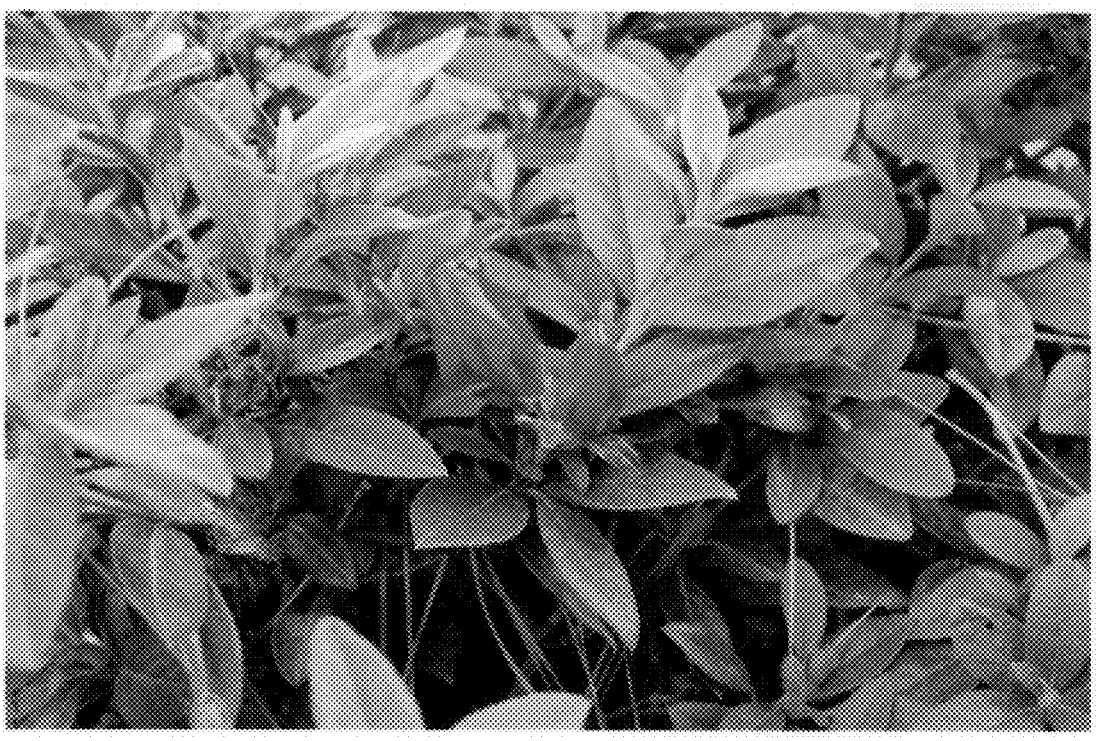
FIG. 3 is a close-up showing flower buds and immature foliage.
Figure 4:
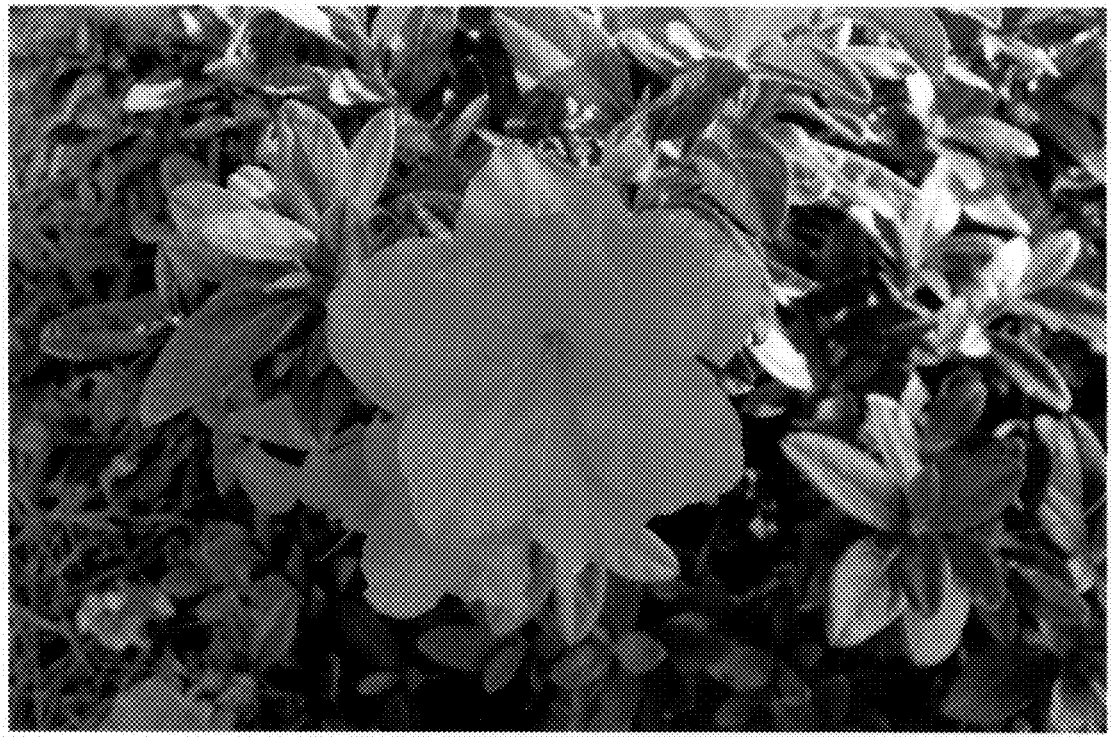
FIG. 4 is a close-up showing flower size, form, and color.

The following is a detailed description of 'MNIHAR011' based on observations made of 4-year-old plants grown in three-gallon containers according to wholesale commercial production conditions, under full-sun; and in an evaluation bed under semi-shade conditions in Dearing, Ga. in the spring, summer, and fall seasons of 2009. The colors of the various plant parts are detailed with reference to The Royal Horticultural Society Colour Chart (2001).

Classification:

*Family*.—Ericaceae.
*Species*.—*Rhododendron* sp.
*Common Name*.—Azalea.
*Commercial Name*.—'MNIHAR011'.

Parentage:

*Female parent*.—The azalea plant 'Conleb' (U.S. Plant Pat. No. 10,581).

*Male parent*.—The azalea plant 'Jay Valentine' (unpatented).

Growth:

*Form*.—Dense, low-growing and compact.

*Texture*.—Medium.

*Height*.—60.96 cm to 91.44 cm.

*Width*.—90.44 cm to 120.92 cm.

*Growth habit*.—Broadly-rounded and freely-branching.

*Growth rate*.—Moderate growth rate under normal fertilization and moisture conditions. In a period of six years from a rooted cutting the plant reaches a height of 60.96 cm and a spread of 90.44 cm. The growth rate is normally about 5 cm to 6 cm per year; the plant reaches a height of 60.96 cm to 91.44 cm at maturity while maintaining a dense habit due to the abundant branch development.

*Spring growth*.—The date of initial spring growth is March 9, followed by continuous growth through fall.

*Life cycle*.—Perennial and evergreen.

Leaves:

*Arrangement*.—Alternate, simple, pubescent, and evergreen.

*Shape*.—Elliptic to broadly elliptic.

*Apex*.—Mucronate.

*Base*.—Acuminate.

*Margin*.—Entire.

*Length*.—4.2 cm.

*Width*.—1.3 cm.

*Venation pattern*.—Pinnate; the mid-veins and laterals are impressed on the upper surface and the prominent on the lower surface.

*Immature leaf*.—Upper surface: Color: Semi-glossy to matte, RHS 144A (yellow-green). Pubescence: Strigose and scabrous mainly along the margin and midvein; color is RHS N157D (white) to RHS 163B (greyed-orange). Lower surface: Color: Semi-glossy to matte, RHS 146C (yellow-green). Pubescence: Mainly strigose along margin and midvein; color is RHS N157D (white).

*Mature leaf*.—Upper surface: Color: Matte to slightly semi-glossy, RHS 147A (yellow-green). Pubescence: Strigose mainly along the margin; color is RHS 165B (greyed-orange); 0.1 cm in length. Lower surface: Color: Matte to slightly semi-glossy, RHS 146A (yellow-green). Pubescence: Strigose; color is RHS 164B (greyed-orange); 0.1 cm in length.

*Petiole*.—Length: 0.3 cm. Diameter: 0.1 cm×2.5 cm. Pubescence: Pattern is strigose, length is 0.075 cm to 0.2 cm and color is RHS N155A (white) and maturing to RHS 163A (greyed-orange). Color: Begins as RHS 59A (red-purple) and matures to RHS 145B (yellow-green).

Stems:

*Form*.—Densely branched.

*Young stems* (1-*year old and younger*).—Color: Distal end: RHS 59A (red-purple) with RHS N155A (white) and RHS 163B (greyed-orange) strigose pubescence. Basal end is RHS 144B (yellow-green) with RHS 146B (grey-orange) pubescence.

*Second-year stems*.—Stem and pubescence color: RHS N199A (grey-brown) and RHS 197A (greyed-green) with RHS 165A (greyed-orange) strigose pubescence. Length: 3.0 cm with occasional stem reaching 26.0 cm in length. Diameter: 0.1 cm to 0.3 cm. Pith: Solid and uniform. Internode length: Average 0.2 cm but can reach 0.7 cm on rapidly growing stems.

Flower buds:

*Arrangement and form*.—Tight; borne in groups of one or two sheathed by a pair of modified leaf bracts.

*Length*.—1.6 cm.

*Width*.—0.4 cm.

*Color*.—Apex: RHS 139A (green). Base: RHS 146B (yellow-green).

*Shape*.—Ovate.

*Apex*.—Acuminate.

*Base*.—Rounded.

*Length* (*at tight bud*).—0.9 cm.

*Diameter* (*at tight bud*).—0.5 cm.

*Color* (*of scales*).—Immature: RHS 145C (yellow-green). Mature: RHS N144C (yellow-green) with areas of RHS 185A (greyed-purple).

*Texture*.—Pubescent; villous pubescence. Pubescence Color: Immature: RHS N155A (white). Mature: RHS 165C (greyed-orange).

*Pedicel*.—Length: 1.0 cm. Diameter: 0.15 cm. Texture: Villous pubescence. Pubescence Color: RHS N155A (white). Color: Apex end: RHS 44D (red). Basal end: RHS 145A (yellow-green).

*Calyx*.—Form and arrangement: Composed of 5 sepals in a cup-shape. Length: 0.5 cm. Width: 0.4 cm. Color: RHS 145A (yellow-green). Pubescence: Villous and some strigose that is RHS N155A (white) in color. Sepals: Shape: Incised broadly elliptical. Apex: Cuspidate to Obtuse. Base: Fused; joined at base to form a cup. Margin: Lobulate. Color (Both upper and lower surface): RHS 145A (yellow-green). Length: 0.5 cm. Width: 0.4 cm.

Flowers:

*Type*.—Imperfect, hose-in hose flowers.

*Shape*.—Open funnel-shaped.

*Flowering habit and period*.—Borne on the current season's growth; 2 to 3 weeks beginning in late March in Dearing, Ga.; flowering resumes in July and continues until frost which can be as late as November or December.

*Lastingness of flowers on the plant*.—4 to 7 days in the sun; 6 to 9 days in the shade.

*Fragrance*.—Absent.

*Diameter*.—5.8 cm.

*Depth*.—4.0 cm.

*Petals*.—Quantity per flower and arrangement: 5 imbricate petals that are fused at the base and remain fused up to 1.0 cm from the base and 2.0 cm from the base for the three petals with spots. Shape: Obovate. Apex: Rounded. Base: Fused. Margin: Entire and wavy. Texture (both upper and lower surfaces): Glabrous. Length (of petals without spots): 4.6 cm. Width (of petals without spots): 2.5 cm. Color: Both the upper and lower surfaces are RHS 47C (red) fading to 48A (red) at senescence; spots on the upper surface of the petals are RHS 46A (red), and the spots on the lower surface of the petals are RHS 53B (red).

Reproductive parts:

*Pistil*.—Quantity and form: Single, non-petaloid. Length: 4.5 cm. Stigma: Color: RHS 53A (red) and RHS 59A (red-purple). Diameter: 0.1 cm. Style color: RHS 52A (red). Ovary: Pubescent, pilose, with 5 locules and is RHS 155C (white).

*Stamens*.—General: Not present.

Fruit:

*Maturity*.—The capsule matures in about 6 months in Dearing, Ga. and the fruit set is low and contains about 100-300 non-winged seeds.

*Length*.—1.8 cm.

*Width*.—0.9 cm.

*Color*.—RHS 146B (yellow-green).

CULTURE

'MNIHAR011' grows well in a wide range of conditions and tolerates sun to shade. 'MNIHAR011' prefers moist, well-drained soil that is rich in organic matter and responds well to mulching and medium applications of fertilizer. 'MNIHAR011' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

In Table 1, the 'MNIHAR011' is compared to parental varieties 'Conleb' (U.S. Plant Pat. No. 10,581) and 'Jay Valentine' (unpatented) and lists the differences between the varieties.

TABLE 1

| Characteristic | 'MNIHAR011' | 'Conleb' | 'Jay Valentine' |
|---|---|---|---|
| Plant Height (Mature) | 60.96 cm to 91.44 cm | 121.92 cm to 152.4 cm | 121.92 cm to 152.4 cm |
| Flower Diameter | 5.8 cm | 6.5 cm | Not available |
| Flower Form | hose-in-hose | Single to semi-double | Single |
| Flower Color | Dark Rose | Red | Red |
| Bloom Period | Late-March to April and July until frost | Spring, summer, and fall | Spring |
| Hardy Zone | 6 | 7 | 6 |
| Stamen Number | 0 | 0 to 9 | 5 |
| Stamen Type | Not present | Petaloid and Non-petaloid | Non-petaloid |

When 'MNIHAR011' is compared to the commercial variety 'Roblen' (U.S. Plant Pat. No. 16,248), 'MNIHAR011' has larger hose-in-hose flowers (5.8 cm in diameter and 4.0 cm in depth) than 'Roblen' (which has the single and semi-double flowers that are 5.08 cm in length and 5.47 cm in depth). Additionally, 'MNIHAR011' produces dark rose colored flowers, while 'Roblen' has bright red flowers.

I claim:

1. A new variety of Azalea plant named 'MNIHAR011' as herein shown and described.

* * * * *